(12) United States Patent
Pisklak

(10) Patent No.: US 8,430,336 B2
(45) Date of Patent: Apr. 30, 2013

(54) FRAGRANCE DISPENSING WICK AND METHOD

(75) Inventor: Thomas J. Pisklak, Cypress, TX (US)

(73) Assignee: Stonewick, Inc., Dallas, TX (US)

( * ) Notice: Subject to any disclaimer, the term of this patent is extended or adjusted under 35 U.S.C. 154(b) by 0 days.

(21) Appl. No.: 12/744,990

(22) PCT Filed: Dec. 4, 2008

(86) PCT No.: PCT/US2008/085581
§ 371 (c)(1),
(2), (4) Date: Aug. 13, 2010

(87) PCT Pub. No.: WO2009/073813
PCT Pub. Date: Jun. 11, 2009

(65) Prior Publication Data
US 2010/0301128 A1    Dec. 2, 2010

Related U.S. Application Data

(60) Provisional application No. 60/992,178, filed on Dec. 4, 2007.

(51) Int. Cl.
*A61L 29/04* (2006.01)
*A24F 25/00* (2006.01)

(52) U.S. Cl.
USPC ............. 239/44; 239/145; 239/326; 222/187

(58) Field of Classification Search ............. 239/44-46, 239/145, 326; 222/187
See application file for complete search history.

(56) References Cited

U.S. PATENT DOCUMENTS

| | | | |
|---|---|---|---|
| 2,277,377 A * | 3/1942 | Warner | 239/45 |
| 4,266,754 A | 5/1981 | Ninomiya et al. | |
| 4,286,754 A | 9/1981 | Jones | |
| 4,648,972 A | 3/1987 | Ullrich et al. | |
| 4,878,615 A | 11/1989 | Losi | |
| 4,883,116 A * | 11/1989 | Seidenberg et al. | 165/104.26 |
| 5,397,759 A * | 3/1995 | Torobin | 502/415 |
| 5,725,152 A * | 3/1998 | Akyu | 239/45 |
| 5,875,968 A | 3/1999 | Miller et al. | |
| 6,899,280 B2 * | 5/2005 | Kotary et al. | 239/34 |
| 7,055,764 B1 * | 6/2006 | Martinez et al. | 239/145 |
| 7,100,841 B2 | 9/2006 | Ivey et al. | |
| 7,281,670 B2 | 10/2007 | Lakatos et al. | |
| 2004/0044110 A1 | 3/2004 | Baay et al. | |
| 2004/0151747 A1 | 8/2004 | Davis et al. | |
| 2005/0272632 A1 | 12/2005 | Moretti et al. | |
| 2005/0284952 A1 | 12/2005 | Davis et al. | |
| 2006/0249593 A1 | 11/2006 | Brown et al. | |

* cited by examiner

*Primary Examiner* — Dinh Q Nguyen
(74) *Attorney, Agent, or Firm* — Winstead PC

(57) ABSTRACT

A wick which comprises a network matrix ceramic that is contacted either directly or indirectly with a liquid composition such as a fragrance-containing composition. The wick absorbs and transports the liquid composition through capillary action, and the composition is subsequently diffused into the surrounding ambient atmosphere.

15 Claims, 1 Drawing Sheet

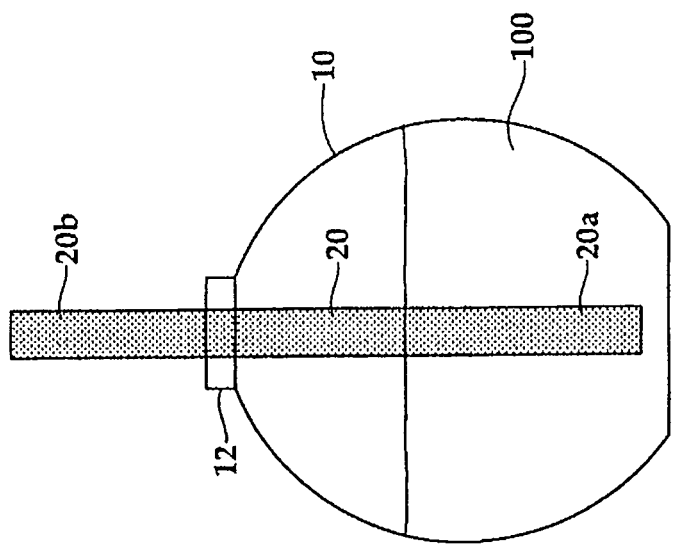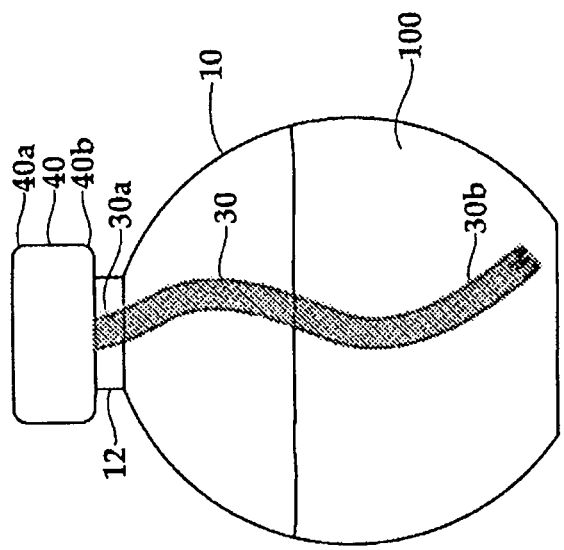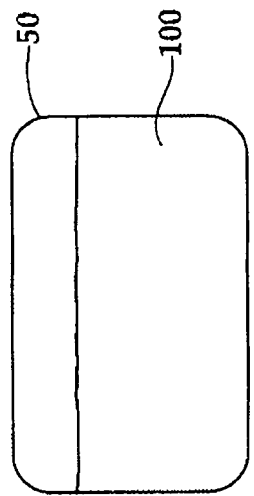

FRAGRANCE DISPENSING WICK AND METHOD

CROSS-REFERENCES TO RELATED APPLICATIONS

This application claims the benefit of U.S. Provisional Application 60/992,178, filed Dec. 4, 2007.

FIELD OF THE INVENTION

The invention relates to a fragrance dispensing wick and related methods.

BACKGROUND OF THE INVENTION

The invention represents an improvement over existing fragrance diffuser systems, otherwise known as "reed diffusers". The aforementioned systems are composed of a number of reeds (usually 5 to 12), fragrance oil, and a fragrance oil reservoir. Reed diffusers deliver fragrance to the atmosphere through the processes of adsorption and desorption (diffusion). For operation, a reservoir is filled, typically half-full, with a fragrance oil composition and reeds are placed in the reservoir. The lower portions of the reeds are submerged in the reservoir and the upper portions are exposed to the atmosphere. The fragrance oil is absorbed into the lower portions of the reeds and travels to the upper portions through capillary action. In this manner the entire length of the reed is saturated with fragrance oil. Once the reeds are saturated, and to some extent during the saturation process, the fragrance oil desorbs from the reeds and diffuses into the surrounding atmosphere, delivering the fragrance.

The reeds are natural products and are typically obtained from rattan, willow, or similar plants which, when dried, are capable of absorbing, wicking, and diffusing liquids. The reeds are typically selected to have a diameter of ~0.10" and are cut to 12.0" lengths.

Since the reeds are natural products, their properties, such as wicking speed, absorption capacity, and shape are inherent to the plant from which they are obtained and cannot be easily modified or optimized for a particular application. Consequently, other than being aesthetically pleasing, the natural reeds are poorly suited for use in fragrance diffusion.

A major limitation of natural reeds is their wicking rate. Other than ambient effects (i.e. air flow, temperature, etc.) the most important factor in the functioning of reed diffusers is the rate at which the fragrance oil is drawn from the reservoir and brought into contact with the ambient atmosphere (wicking rate). Once the reeds are placed in the fragrance oil, it typically requires 36-48 hours for the reeds to become totally saturated and to function at full capacity. This slow wicking rate ($3.2 \times 10^{-2}$ ml/hour) negatively affects the reeds functionality as a fragrance diffusing device. Another important factor in fragrance diffusing is the amount of fragrance oil that is in contact with the surrounding atmosphere. This parameter is controlled by the surface area, and more importantly the surface area to volume ratio, of the diffusing device. Natural reeds have an extremely low surface area to volume ratio (0.064 $cm^2/cm^3$ (lateral surface area/volume)), which is also a factor in their poor functionality. Also, the shape of the reeds is limited to a cylindrical shape due to the morphology of the plant from which they are obtained, which results in a relatively unchangeable surface area to volume ratio. These combined limitations result in a poor rate of fragrance diffusion of ~0.09 g/hr per reed (1.08 g/hr for the typical set of 12). Finally, the slow diffusion rate results in higher manufacturing costs due to the need for increased fragrance concentration in the fragrance oil. To compensate for the low diffusion rate, the fragrance, which is the most costly portion of the fragrance oil, is typically maintained at 15 wt % of the reed diffuser fragrance oil composition.

Standard porous ceramics, such as porous cordierite, have been used in various fragrance diffusion systems. However, they have seen limited use due to low wicking rates and their innate brittleness when formed into shapes with a high aspect ratio. To be effective at absorbing liquids, such as fragrance oils, the ceramic body must be highly porous. Unfortunately, higher porosity also leads to decreased strength of the ceramic body. To be used effectively as a wick, porous ceramics should have an open porosity of greater than 40% of the ceramic body, however, once the porosity is greater than ~30%, the ceramic body is too weak to be used as a wick. Additionally, even with >40% porosity, the wicking rate is exceptionally slow ($2.0 \times 10^{-2}$ mL/hour). These limitations make conventional porous ceramics unsuitable for use as wicks.

Recently, there has been increased interest in providing reed diffuser fragrance formulations that are environmentally friendly. Currently, the majority of reed diffuser formulations use industrial organic solvents such as petroleum distillates and other volatile organic compounds (VOC), which are restricted by CARB (California Air Resources Board). In addition to meeting governmental regulations, reducing or eliminating the use of these solvents would greatly enhance the environmental friendliness of the reed diffuser fragrance formulations. One method to achieve this goal is to use water, instead of organic solvents, as the base of the reed diffuser fragrance formulations. With the aid of surfactants to dissolve the fragrance in water this can be achieved. However, wooden reed diffusers are not compatible with water based formulations. When water based formulations are used with wooden reed diffusers the diffusers become water-logged and, consequently, the wicking rate is severely reduced. In addition to retarding the wicking rate, the water encourages the growth of mold and mildew on the wooden diffusers and causes them to decay. Likewise, conventional porous ceramics do not perform adequately with water based formulations, because their low wicking rate renders them virtually unusable as fragrance diffusers.

In short, the main limitations of the current technology, whether it be wooden diffusers or conventional porous ceramics, is their low wicking rates and inability to effectively utilize water-based fragrance formulations. To overcome the limitations associated with natural reed and conventional porous ceramic fragrance diffusers, a wick made of a network matrix ceramic having a high wicking rate with aqueous, water-based formulations as well as non-aqueous organic formulations, and having higher strength than conventional porous ceramics, was developed. The present invention is directed to such a wick.

SUMMARY OF THE INVENTION

An aspect of the invention is directed to a fragrance dispensing device which comprises a reservoir having an open end, wherein the reservoir contains a quantity of a liquid composition containing a fragrance; and a wick comprising a network matrix ceramic, the wick having a first end that contacts the open end of the reservoir, and a second end in contact with the liquid composition.

Another aspect of the invention is directed to a method for delivering a fragrance to an ambient environment which comprises the step of providing a fragrance dispensing device which comprises a reservoir having an open end, wherein said reservoir contains a quantity of a liquid composition containing a fragrance; and a wick which comprises a network matrix ceramic, the wick having a first end that contacts the open end of the reservoir, and a second end in contact with the liquid composition.

A further aspect of the invention is directed to a wick which comprises a network matrix ceramic, the wick having a first end and a second end, wherein the second end of the wick contacts a liquid composition containing a fragrance.

Another embodiment of the invention is directed to a wick which comprises a network matrix ceramic, the wick having a first end and a second end, wherein the second end of the wick is removably connected to a secondary wicking material. In certain embodiments of the invention, the secondary wicking material is in contact with a liquid composition containing a fragrance.

A further embodiment of the invention is directed to a wick which comprises a network matrix ceramic, wherein the wick is a reservoir for a liquid composition containing a fragrance.

BRIEF DESCRIPTION OF THE DRAWINGS

FIG. 1 shows a wick according to the invention having a lower portion that extends into a fragrance-containing composition and an upper portion that extends into the atmosphere.

FIG. 2 shows a wick according to the invention that is in communication with a fragrance-containing composition via a secondary wicking material.

FIG. 3 shows a wick according to the invention where the fragrance composition is contained within the body of the ceramic diffuser.

DETAILED DESCRIPTION OF EXEMPLARY EMBODIMENTS

In general, the present invention relates to a wick composed of a network matrix ceramic. The wick absorbs and transports a fragrance composition through capillary action, and fragrance is subsequently diffused into the surrounding atmosphere. The wick is composed of inorganic binders and ceramic particles.

Utilizing a network matrix ceramic to construct a wicking device overcomes three major limitations associated with conventional porous ceramics. First, conventional porous ceramics are formed by adding a pore forming agent, such as carbon, to a ceramic mixture prior to firing. During the firing process, the pore former is pyrolized and leaves voids in the finished ceramic body. However, when enough pore former is added to the ceramic composition to achieve the required porosity (~40%) the finished ceramic body is greatly weakened. Second, a surface with high silica ($SiO_2$) content (>50%) is required to effectively increase the wicking speeds of fragrance formulations. Normally, this high silica content would be achieved by adding a high percentage of glassy compounds to the ceramic mixture. However, when high silica content is coupled with a large percentage of pore formers, the ceramic shrinks and flows considerably during calcination, making the formation of precise shapes extremely difficult. Additionally, because glassy compounds become viscous and flow at the required temperatures for calcination, it is difficult to maintain porosity, due to backfilling of the pores by the viscous ceramic. Third, because conventional ceramics are mostly homogenous, single phase systems after calcination, it is difficult to maximize opposing properties. For example, a ceramic with high silica content exhibits high wicking rates but is much weaker than a ceramic with high alumina content. Blending the two together in a homogenous ceramic body produces a ceramic with relatively low wicking rates and relatively low strength.

Network matrix ceramics are composed of two phases and are much more versatile than conventional ceramics. Typically, one phase forms the main body (ceramic particles), while a second phase (binder) encapsulates and connects the ceramic particles to one another. To form a network matrix ceramic body, pre-calcined ceramic particles are mixed with a binder composition which melts and becomes viscous at a lower temperature than the ceramic particles. During calcination, the ceramic composition is heated to a sufficient temperature to viscosity the binder but not high enough to affect the ceramic particles. At this point, the viscous component is wicked between and around the ceramic particles, forming ceramic bridges which connect the particles to form a single mass. The amount of binder is carefully controlled so that there is enough present to encapsulate and connect the particles, but not enough to fill the voids between particles. In this manner, an open network monolith is formed.

The versatility of this system allows for the majority of the wick to be composed of high strength aluminosilicate ceramic, while the surface can have a high silica content that promotes high wicking rates. Furthermore, unlike conventional ceramics, the amount of void space present in the network ceramic can be controlled in several different ways. First, the void space present is dependant, to some extent, upon the packing characteristics of the ceramic particles. To produce a large amount of void space, irregularly shaped ceramic particles are used, so that inter-particle distance is maximized. To produce a small amount of void space, spherical particles with a low range of particle size distributions are used, so that inter-particle distance is minimized. Second, the amount of inorganic binder present affects the amount of void space created in the ceramic. The inorganic binder can be varied from a small percentage of the total formulation, which forms a large amount of void space, to a large percentage of the total formulation, which forms a thick coating on the particles and fills in excess void space. Third, traditional pore formers, such as carbon, can be used in a manner similar to conventional ceramics.

The binder may be any material which has a high melting point (>250° C.), but whose melting or sintering point is lower than that of the other components. This may include materials such as bentonite, hectorite, laponite, montmorillonite, ball clay, meta-kaolin, palygorskite (attapulgite), barasym SSM-100 (synthetic mica-montmorillonite), ripidolite, rectorite, optigel SH (synthetic hectorite), illite, nontronite, illite-smectite, sepiolite, beidellite, cookeite, or generally any type of clay, borosilicate glass, aluminosilicate glass, glass fibers, or feldspars. The binder may also be a combination of two or more of these components.

The pre-formed ceramic particles may range in diameter between 1.0 and 1000 microns, but preferably is 300 microns. The pre-formed ceramic particles may be composed of any material that has a melting or sintering point higher than the binder material, such as (hut not limited to): perovskites, bentonite, hectorite, laponite, montmorillonite, ball clay, meta-kaolin, palygorskite(attapulgite), barasym SSM-100 (synthetic mica-montmorillonite), ripidolite, zeolites, rectorite, optigel SH (synthetic hectorite), illite, nontronite, illite-smectite, sepiolite, beidellite, cookeite, or generally any type of clay. The particles may also be composed of such materials as talc, aluminum oxide, rutile, anatase, metals, metal oxides, zeolites, mullite, silica, wollastonite, ilmenite, dolomite, or any synthetic or naturally occurring mineral, or porcelain, silicon nitride, zirconia, steatite or wollastonite. The ceramic particles may also be a combination of two or more of these components.

Typically, the ceramic particles are formed, sintered, and sized prior to mixing with binder. The ceramic particles are selected to have a small particle size distribution, such that all particles are similar in size.

The wick can be composed of 15-50% inorganic binder and 50-85% refractory particles, but preferably 30 wt % binder and 70 wt % refractory particles. The binder is not limited to a single component but may be a mixture of two or more binders, such as 40% glass and 60% bentonite. Likewise, the ceramic particles are not limited to a single component, but may be a mixture of two or more components, for example kaolinite and zeolite.

After mixing the components a wick is formed in the desired shape through extrusion, die casting, or other techniques known in the art. In an embodiment of the invention, as seen in FIG. 1, the wick 20 may be cylindrical, but is not limited to this shape. The wick can be constructed in any shape that increases its surface area, or a shape that is suited to a particular application such as (but not limited to): a round, spherical, cylindrical, square, hexagonal, or cubic wick.

After forming the desired shape the wick monolith is sintered in a furnace to fuse the ceramic particles. The monolith is typically sintered between 500° C. and 1500° C., but preferably at 1000° C.

An aspect of the invention is directed to a fragrance dispensing device which comprises a reservoir having an open end, wherein said reservoir contains a quantity of a liquid fragrance composition; and a wick which comprises a network matrix ceramic, the wick having a first end that contacts the open end of the reservoir, and a second end in contact with the liquid composition.

Another aspect of the invention is directed to a method for delivering a fragrance to an ambient environment which comprises the step of providing a fragrance dispensing device which comprises a reservoir having an open end, wherein said reservoir contains a quantity of a liquid fragrance composition; and a wick which comprises a network matrix ceramic, the wick having a first end that contacts the open end of the reservoir, and a second end in contact with the liquid fragrance composition.

A further aspect of the invention is directed to a wick which comprises a network matrix ceramic, the wick having a first end and a second end, wherein the second end of the wick contacts a liquid fragrance composition.

As seen in FIG. 1, after sintering, the wick 20 is placed in a reservoir 10 containing a fragrance composition 100 where the lower portion 20a of the wick 20 is in contact with the fragrance composition 100. The wick 20 is allowed to remain in a free-standing position without the need for any support. The upper portion 20b of the wick 20 extends out of the open neck portion 12 of the reservoir 10. The fragrance composition 100 is absorbed by the wick and travels up its length via capillary action. The fragrance composition is subsequently desorbed, or diffused, from the upper portion of the wick 20 into the surrounding ambient environment.

Another embodiment of the invention is directed to a wick which comprises a network matrix ceramic, the wick having a first end and a second end, wherein the second end of the wick is removably connected to a secondary wicking material. The second end of the wick is connected to a first end of the secondary wicking material. In certain embodiments of the invention, a second end of the secondary wicking material is in contact with a liquid composition.

In an embodiment of the invention, as seen in FIG. 2, the wick 40 is shown having a first end 40a that is located at an opposite end from the open neck end 12 of the reservoir 10, and a second end 40b that contacts the open neck 12. The second end 40b of the wick 40 is removably connected to a secondary wicking material 30 through a first end 30a. A second end 30b of the secondary wicking material 30 is in contact with the fragrance composition 100 contained within the reservoir 10. The secondary wicking material 30 may be composed of any material that is capable of wicking the fragrance composition 100, such as (but not limited to): cotton cloth, cotton-synthetic blend, synthetic wicking materials, or porous ceramic.

A further embodiment of the invention is directed to a wick which comprises a network matrix ceramic, wherein the wick is a reservoir for a liquid fragrance composition.

As seen in FIG. 3, the network matrix ceramic may be formed into a larger, low aspect ratio, shaped monolith 50 and pre-filled with fragrance oil 100. The fragrance composition 100 enters into the pores of the network matrix ceramic monolith 50, and is dispersed gradually over time. The network ceramic may be formed into other shapes as well, such as (but not limited to): decorative shapes, flower shape, natural stone shape, pyramidal, spherical, or cubic. In this case, the fragrance composition is contained within the void space of the network ceramic which becomes a portable fragrance diffuser. Over time, the fragrance composition diffuses out of the shaped network ceramic monolith until the majority of the fragrance oil has diffused through, at which time, the shaped monolith can be refilled. The refilling process may include an injection step to introduce the fragrance composition 100 into the monolith 50. Alternately, the monolith 50 may be soaked in a fragrance composition for a specified length of time to allow the fragrance composition to enter into the void space of the network ceramic.

Diffusers formed from the network matrix ceramic material exhibit enhanced fragrance diffusion when compared with conventional reed diffusers. Unlike natural reed diffusers the ceramic material can be formed or fashioned into almost any shape to enhance functionality as well as aesthetic appeal. When produced in a similar shape (cylindrical, diameter=0.25 inches, length=10 inches) network matrix ceramic monoliths formed from mullite ceramic particles with metakaolin and glass as the binder, show enhanced fragrance diffusion with a non-aqueous fragrance oil base relative to natural reed diffusers (Table 1). The network ceramics have a typical wicking rate of 3.6 ml/hr, which is 112 times greater than the natural reed diffusers ($3.2 \times 10^{-2}$ ml/hr). Also, these porous ceramic diffusers have a surface area to pore volume ratio of 0.16 $cm^2/cm^3$, which is 2.5 times greater than the natural reed diffusers (0.064 $cm^2/cm^3$). Consequently, the overall functionality of the network matrix ceramic monolith is greater than that of the natural reed diffusers. The network matrix ceramic wicks or diffusers exhibit a fragrance diffusion rate of 0.25 g/hr while that of the natural reeds is only 0.09 g/hr.

TABLE 1

| Reed Material | Fragrance Base | Wicking Rate (ml/h) | Diffusion Rate (g/h) | Break Point (g) |
|---|---|---|---|---|
| Network Composite | | | | 347 |
| | Aqueous | 14.4 | 0.86 | |
| | Non-Aqueous | 3.6 | 0.25 | |
| Wood | | | | — |
| | Aqueous | — | — | |

TABLE 1-continued

| Reed Material | Fragrance Base | Wicking Rate (ml/h) | Diffusion Rate (g/h) | Break Point (g) |
|---|---|---|---|---|
| Corderite | Non-Aqueous | 0.032 | 0.09 | 321.5* |
| | Aqueous | 0.053 | 0.07 | |
| | Non-Aqueous | 0.019 | 0.05 | — |

*normalized to 49% porosity

Due to the higher diffusion rate of the network matrix ceramic monoliths, the fragrance oil composition require much less fragrance in the fragrance oil formulation to match the fragrancing power of a reed diffuser.

Likewise, wicks formed from the network matrix ceramic material exhibit enhanced fragrance diffusion when compared with conventional porous ceramic diffusers. Unlike ceramic diffusers, the network matrix ceramic material can be easily and economically formed or fashioned into almost any shape or composition to enhance functionality as well as aesthetic appeal. When produced in a similar shape (cylindrical, diameter=0.25 inches, length=10 inches) network matrix ceramic monoliths formed from mullite ceramic particles with meta-kaolin and glass as the binder, show enhanced fragrance diffusion relative conventional porous ceramic diffusers with non-aqueous and aqueous fragrance oil bases (Table 1). The network matrix ceramics exhibit wicking rates of 14.4 ml/h and 3.6 ml/h for aqueous and non-aqueous fragrance bases, respectively, while porous ceramics wick rates are only 0.05 ml/h and 0.02 ml/h for aqueous and non-aqueous fragrance bases, respectively. Consequently, the overall functionality of the network matrix ceramic monolith is greater than that of the conventional porous ceramic diffusers. For aqueous fragrance bases, the network matrix ceramic monoliths exhibit a fragrance diffusion rate of 0.86 g/h while that of the conventional porous ceramics is only 0.07 g/h. For non-aqueous fragrance bases, the network matrix ceramic monoliths exhibit a fragrance diffusion rate of 0.25 g/h while that of the conventional porous ceramics is only 0.05 g/h.

The utility of the present invention is not necessarily limited to household fragrance diffusion, but may exhibit improved performance over existing state-of-the-art in other applications as well. For example, a network matrix monolith can be used as the wick portion of an apparatus for dispensing fragrance into the interior of automobiles.

Another example of the utility present invention is as a self contained fragrancing apparatus, wherein there is no external liquid reservoir, but the liquid fragrance formulation in contained within the void space of the network matrix ceramic.

Another example of the utility of the present invention is as a liquid transporting device for the transport of liquid from one location to another wherein the transfer rate is controlled by the wicking rate of the network matrix ceramic.

Another example of the utility of the present invention is for the controlled diffusion of compounds which repel insects and parasites. In this embodiment, the liquid reservoir contains a formulation of compounds, such as N,N-diethyl-meta-toluamide (DEET), which are designed to repel insects. The controlled diffusion of such compounds into the surrounding environment by the network matrix ceramic would effectively repel insects and parasites over a long period of time.

Another example of the utility of the present invention is for the controlled diffusion of antibacterial compounds which combat bacteria growth. In this embodiment, the liquid reservoir would contain a formulation of compounds, such as 3,4,4'-trichlorocarbanalide (TCC), which are designed to retard bacterial growth. The controlled diffusion of such compounds into the surrounding environment by the network matrix ceramic would effectively combat bacterial growth over a long period of time.

WORKING EXAMPLES

Example 1

Mullite/Clay Network Matrix Ceramic Wick

A network matrix ceramic was formed using Mullite ($3Al_2O_3.2SiO_2$) with a nominal particle size of 300 microns as the ceramic particle and meta-kaolin as the binder. To form the monolith, 84.0 grams of Mullite were mixed with 36.0 grams of meta-kaolin (70 wt %, and 30 wt %, respectively). The two powders were thoroughly mixed, followed by the addition of 6.0 grams of carboxy methylcellulose (CMC) and 40.0 grams of $H_2O$. CMC is an organic binder which helps the mixture retain its shape after extrusion. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic monolith with a diameter of 0.25" and a length of 10.0".

Example 2

Mullite/Glass Network Matrix Ceramic Wick

A network matrix ceramic was formed using Mullite ($3Al_2O_2.2O_2$) with a nominal particle size of 300 microns as the ceramic particle and glass as the binder. To form the monolith, 84.0 grams of Mullite (300 μm) were mixed with 36.0 grams of glass (70 wt %, and 30 wt %, respectively). The two powders were thoroughly mixed, followed by the addition of 6.0 grams of carboxy methylcellulose (CMC) and 40.0 grams of $H_2O$. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic wick with a diameter of 0.25" and a length of 10.0".

Example 3

Alumina/Glass Network Matrix Ceramic Wick

The network matrix ceramic was composed of alumina ($Al_2O_3$) with nominal particle sizes of ~90 microns. To form the wick, 84.0 grams of alumina were mixed with 36.0 grams of glass (70 wt %, and 30 wt %, respectively). The two powders were thoroughly mixed, followed by the addition of 6.0 grams of carboxy methylcellulose (CMC) and 40.0 grams of $H_2O$. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic wick with a diameter of 0.25" and a length of 10.0".

Example 4

Mullite/Clay/Glass Network Matrix Ceramic Wick

A network matrix ceramic monolith was formed using Mullite ($3Al_2O_3.2SiO_2$) with a nominal particle size of 300 microns as the ceramic particle and a 1:1 mixture of meta-kaolin and glass as the binder. To form the monolith, 84.0 grams of Mullite (300 μm) were mixed with 18.0 grams of meta-kaolin and 18.0 grams of glass (70 wt %, 15 wt %, 15 wt %, respectively). The three powders were thoroughly mixed, followed by the addition of 6.0 grams of carboxy methylcellulose (CMC) and 40.0 grams of $H_2O$. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic with a diameter of 0.25" and a length of 10.0".

Example 5

Mullite/Clay/Glass/Carbon (15%) Network Matrix Ceramic Wick

Charcoal (particle size=50 μm) was added to the composition to increase the macroporosity of the network matrix ceramic monoliths. To form the monolith, 72.0 grams of Mullite (300 μm) were mixed with 15.0 grams of meta-kaolin, 15.0 grams of glass, and 18.0 grams of charcoal (60 wt %, 13 wt %, 13 wt %, and 15 wt %, respectively). The four powders were thoroughly mixed, followed by the addition of 6.0 grams of carboxy methylcellulose (CMC) and 50.0 grams of $H_2O$. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic wick with a diameter of 0.25" and a length of 10.0".

Example 6

Mullite/Clay/Glass/Carbon (25%) Network Matrix Ceramic Wick

Charcoal (particle size=50 μm) was added to the composition to increase the macroporosity of the wick. To form the wick, 70.0 grams of Mullite (300 μm) were mixed with 15.0 grams of meta-kaolin, 15.0 grams of glass, and 33.0 grams of charcoal (53 wt %, 11 wt %, 11 wt %, and 25 wt %, respectively). The four powders were thoroughly mixed, followed by the addition of 6.0 grams of carboxy methylcellulose (CMC) and 50.0 grams of $H_2O$. This mixture was thoroughly mixed and extruded in a cylindrical shape. The cylinder was placed in a convection oven at 30° C. and allowed to dry overnight. The dried cylinder was then placed in a furnace and heated at 1000° C. for 2 hours to form the completed network matrix ceramic wick with a diameter of 0.25" and a length of 10.0".

Example 7

Non-Aqueous Wicking Rate

To determine the wicking rate (Table 1) of wooden reeds, conventional porous ceramic, and network matrix ceramic with non-aqueous fragrance formulations, a standard test was performed using 3-methoxy-3-methyl-1-butanol as the fragrance base. To simulate standard reed diffuser formulations, 450 grams of 3-methoxy-3-methyl-1-butanol was mixed with 50 grams of neat fragrance oil. A 600 mL, container was loaded with 200 grams of the fragrance oil formulation. A single reed (either wooden, porous ceramic, or network matrix ceramic) was placed in the container and the time was recorded. Finally, the time at which the liquid reached the top of the reed was recorded. The distance traveled was measured from the top of liquid in the container to the top of the reed. The distance, in cm, was divided by the time (in hours) to give the flow velocity in cm/h. To convert this velocity to volumetric flow rate the following equation was used:

$$V = A \times v$$

A is the cross-sectional area of the reed, v is the average flow velocity, and V is the volumetric flow rate or wicking rate.

For wicking rate tests, wooden reeds were obtained from a commercial reed diffuser set (Target, Inc.). A conventional porous ceramic reed was made by forming a standard cordierite precursor powder and adding 30% carbon black as a pore former. The mixture was extruded into a 0.25"×10" cylinder and calcined at 1290° C. for 5 hours to obtain a cordierite reed with 30% porosity. A network matrix ceramic was formed following the procedure in Example 5 to form a 0.25"×10" cylinder with 49% porosity.

Example 8

Aqueous Wicking Rate

To determine the wicking rate (Table 1) of wooden reeds, conventional porous ceramic, and network matrix ceramic with aqueous fragrance formulations a standard test was performed using water as the fragrance base. The aqueous fragrance formulation was composed of 4% neat fragrance, 4% surfactant, and 92% water. A 600 mL container was loaded with 200 grams of the aqueous fragrance formulation. A single reed (either wooden, porous ceramic, or network matrix ceramic) was placed in the container and the time was recorded. Finally, the time at which the liquid reached the top of the reed was recorded. The distance traveled was measured from the top of liquid in the container to the top of the reed. The distance, in cm, was divided by the time (in hours) to give the flow velocity in cm/hr. The equation in Example 7 was used to convert the flow velocity to volumetric flow rate (wicking rate).

Example 9

Non-Aqueous Fragrance Formulation Diffusion Rate

To determine the fragrance diffusion rate (Table 1) of wooden reeds, conventional porous ceramic, and network matrix ceramic with non-aqueous fragrance formulations a standard test was performed using 3-methoxy-3-methyl-1-butanol as the fragrance base. To simulate standard reed diffuser formulations, 450 grams of 3-methoxy-3-methyl-1-butanol was mixed with 50 grams of neat fragrance oil. A 600 mL container was loaded with 200 gams of the non-aqueous fragrance formulation. A single reed (either wooden, porous ceramic, or network matrix ceramic) was placed in the container and the time was recorded. The container was then placed on a balance and tared. After 4 hours the amount of fragrance formulation which had evaporated was recorded. The amount of fragance formulation which evaporated, in grams, was divided by the time, in hours, to give the diffusion rate.

For diffusion rate tests, wooden reeds were obtained from a commercial reed diffuser set (Target, Inc.). A conventional porous ceramic reed was made by forming a standard cordierite precursor powder and adding 30% carbon black as a pore former. The mixture was extruded into a 0.25"×10" cylinder and calcined at 1290° C. for 5 hours to obtain a cordierite reed with 30% porosity. A network matrix ceramic was formed following the procedure in Example 5 to form a 0.25"×10" cylinder with 49% porosity.

Example 10

Aqueous Fragrance Formulation Diffusion Rate

To determine the fragrance diffusion rate (Table 1) of wooden reeds, conventional porous ceramic, and network matrix ceramic with aqueous fragrance formulations a standard test was performed using water as the fragrance base. The aqueous fragrance formulation was composed of 4% neat fragrance, 4% surfactant, and 92% water. A 600 mL container was loaded with 200 grams of the aqueous fragrance formulation. A single reed (either wooden, porous ceramic, or network matrix ceramic) was placed in the container and the time was recorded. The container was then placed on a balance and tared. After 4 hours the amount of fragrance formulation which had evaporated was recorded. The amount of fragrance formulation which evaporated, in grams, was divided by the time, in hours, to give the diffusion rate.

Example 11

Strength Tests

To determine the strength of the ceramic wicks a strength test was developed to determine the point at which the wicks break (Table 1). To perform the break point tests, a conventional porous ceramic wick was made by forming a standard cordierite precursor powder and adding 30% carbon black as a pore former. The mixture was extruded into a 0.25"×10" cylinder and calcined at 1290° C. for 5 hours to obtain a cordierite wick with 30% porosity. For the network matrix ceramic, the procedure in Example 5 was followed to form a 0.25"×10" cylinder with 49% porosity. The wicks were clamped to a lab bench with 8" of the wick hanging over the edge. Weights (20 g) were incrementally added to the end of the wick until the wick broke. Although it would be ideal to compare wicks of the same porosity, the conventional porous ceramic was too weak at 49% porosity to perform the tests. Therefore, the break point was performed at 30% porosity and normalized, mathematically to 49%.

It will be obvious to those skilled in the art that the invention described here can be essentially duplicated by making minor changes in the material content or the method of manufacture. Therefore, the present invention is well adapted to carry out the objects and attain the ends and advantages mentioned as well as those which are inherent therein. While the invention has been depicted and described by reference to embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention.

What is claimed is:

1. A fragrance dispensing device which comprises:
 a reservoir having an open end, wherein said reservoir contains a quantity of a liquid composition; and
 a wick which comprises a network matrix ceramic, the wick having a first end that contacts the open end of the reservoir, and a second end in contact with the liquid composition, and wherein the network matrix ceramic is composed of two phases, wherein the first phase is composed of sintered ceramic particles and the second phase is composed of an inorganic binder having a melting point greater than 250° C. and selected from the group consisting of bentonite, hectorite, laponite, montmorillonite, meta-kaolin, attapulgite, synthetic mica-montmorillonite, ripidolite, rectorite, synthetic hectorite, illite, nontronite, illite-smectite, sepiolite, beidellite, cookeite, clay, borosilicate glass, aluminosilicate glass, glass fibers, and feldspars, wherein the second phase encapsulates and connects the first phase.

2. The fragrance dispensing device according to claim 1 wherein the liquid composition is a fragrance material.

3. The fragrance dispensing device according to claim 1 wherein the liquid composition is an insect repellent composition.

4. The fragrance dispensing device according to claim 1 wherein the liquid composition is a deodorizing composition.

5. The fragrance dispensing device according to claim 1 wherein the liquid composition is a medicinal compound.

6. The fragrance dispensing device according to claim 1 wherein the liquid composition is an herbal composition.

7. The fragrance dispensing device according to claim 1 wherein the liquid composition is a disinfectant composition.

8. The fragrance dispensing device according to claim 1 wherein the liquid composition is an aqueous composition.

9. The fragrance dispensing device according to claim 1 wherein the liquid composition is a non-aqueous composition.

10. The fragrance dispensing device according to claim 1 wherein the liquid composition is a mixture of an aqueous composition and a non-aqueous composition, 11. A method for delivering a fragrance to an ambient environment which comprises the step of:
 providing a fragrance dispensing device according to claim 1.

12. A wick which comprises a network matrix ceramic, the wick having a first end and a second end, wherein the second end of the wick contacts a liquid composition, wherein the network matrix ceramic is composed of two phases, wherein the first phase is composed of sintered ceramic particles and the second phase is composed of an inorganic binder having a melting point greater than 250° C. and selected from the group consisting of bentonite, hectorite, laponite, montmorillonite, meta-kaolin, attapulgite, synthetic mica-montmorillonite, ripidolite, rectorite, synthetic hectorite, illite, nontronite, illite-smectite, sepiolite, beidellite, cookeite, clay, borosilicate glass, aluminosilicate glass, glass fibers, and feldspars, wherein the second phase encapsulates and connects the first phase.

13. A wick which comprises a network matrix ceramic, the wick having a first end and a second end, wherein the second end of the wick is removably connected to a secondary wicking material, wherein the network matrix ceramic is composed of two phases, wherein the first phase is composed of sintered ceramic particles and the second phase is composed of an inorganic binder having a melting point greater than 250° C. and selected from the group consisting of bentonite, hectorite, laponite, montmorillonite, meta-kaolin, attapulgite, synthetic mica-montmorillonite, ripidolite, rectorite, synthetic hectorite, illite, nontronite, illite-smectite, sepiolite, beidellite, cookeite, clay, borosilicate glass, aluminosilicate glass, glass fibers, and feldspars, wherein the second phase encapsulates and connects the first phase.

14. The wick according to claim 13, wherein the secondary wicking material is in contact with a liquid composition.

15. A wick which comprises a network matrix ceramic, wherein the wick is a reservoir for a liquid composition, wherein the network matrix ceramic is composed of two phases, wherein the first phase is composed of sintered ceramic particles and the second phase is composed of an inorganic binder having a melting point greater than 250° C. and selected from the group consisting of bentonite, hectorite, laponite, montmorillonite, meta-kaolin, attapulgite, synthetic mica-montmorillonite, ripidolite, rectorite, synthetic hectorite, illite, nontronite, illite-smectite, sepiolite, beidellite, cookeite, clay, borosilicate glass, aluminosilicate glass, glass fibers, and feldspars, wherein the second phase encapsulates and connects the first phase.

* * * * *